United States Patent [19]

Hsu

[11] Patent Number: 5,102,898
[45] Date of Patent: Apr. 7, 1992

[54] BENZOXAZOLONE COMPOUNDS AND THE USE THEREOF AS MICROBICIDES

[75] Inventor: Adam C. Hsu, Lansdale, Pa.

[73] Assignee: Rohm and Haas Company, Philadelphia, Pa.

[21] Appl. No.: 697,655

[22] Filed: May 8, 1991

Related U.S. Application Data

[63] Continuation-in-part of Ser. No. 433,862, Nov. 9, 1989, abandoned.

[51] Int. Cl.$^5$ .................... C07D 263/50; A01N 43/76
[52] U.S. Cl. .......................................... 514/375; 71/67; 548/221
[58] Field of Search .............. 514/375; 548/221; 71/67

[56] References Cited

U.S. PATENT DOCUMENTS

| | | | |
|---|---|---|---|
| 2,769,010 | 10/1956 | D'Amico | 548/221 |
| 3,136,689 | 6/1964 | Miller | 514/375 |
| 4,670,451 | 6/1987 | Uematsu et al. | 514/375 |
| 4,675,370 | 6/1987 | Tar et al. | 548/224 |
| 4,786,310 | 11/1988 | Haga et al. | 71/90 |
| 4,828,605 | 5/1989 | Haga et al. | 71/90 |
| 4,990,525 | 2/1991 | Hsu | 71/69 |

FOREIGN PATENT DOCUMENTS 194354 2/1982 Czechoslovakia .

OTHER PUBLICATIONS

Chemical Abstract 97:23779c.
J. Pharm. Sc. 57,1763 (1968), Sam et al.
Chemical Abstract 89:179902h (1978).
Chemical Abstract 94:192196d (1980).

Primary Examiner—Donald G. Daus
Attorney, Agent, or Firm—Michael B. Fein

[57] ABSTRACT

Novel compounds of the formula

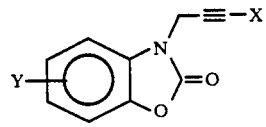

wherein
X is I or Br; and
Y is independently selected from the group consisting of H, halogen, $NO_2$, ($C_1$-$C_4$) alkyl, ($C_1$-$C_4$) alkoxy, CN, OCO ($C_1$-$C_4$) alkyl, OCOPh or halo ($C_1$-$C_4$) alkyl, are disclosed as having microbicidal activity.

11 Claims, No Drawings

BENZOXAZOLONE COMPOUNDS AND THE USE THEREOF AS MICROBICIDES

This is a continuation-in-part of Ser. No. 07/433,862, filed Nov. 9, 1989, which will be abandoned.

BACKGROUND OF THE INVENTION

1. Field of the Invention

This invention concerns novel benzoxazolones containing a halosubstituted alkyne group, and the use of such compounds as microbicides. More specifically, the compounds to which the invention is directed have the formula (I)

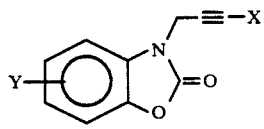

(I)

where
X = I or Br, and
Y = is independently selected from the group consisting of H, halogen, $NO_2$, ($C_1$-$C_4$)alkyl, ($C_1$-$C_4$)alkoxy, CN, OCO ($C_1$-$C_4$)alkyl, OCOPh or halo ($C_1$-$C_4$)alkyl.

As used hereinafter the term "microbicide" (or "biocide") is intended to include, but is not restricted to, bactericides, fungicides and algicides, and microbicidal activity refers to both the elimination of and also to the inhibition or prevention of growth of microbial organisms such as bacteria, fungi and algae.

2. Prior Art

Compounds having the formula

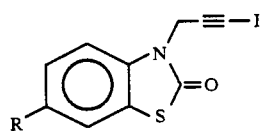

where R is H, Cl or $NO_2$ are disclosed in Czech Patent No. 194354 (Chem Abs. 97:23779c), and are said to have antifungal activity. European patent application No. 230874A discloses related compounds having the formula

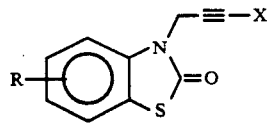

where X = H or Br: these compounds are said to have herbicidal activity. Neither document mentions benzoxazolones.

Benzoxazolones having the formula

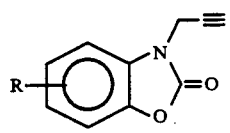

are disclosed in J. Pharm. Sc., 57, 1763 (1968), Chem. Abs. 89:179902h and Chem abs 94:192196d; however no microbicidal activity is mentioned in any of the disclosures. Chem Abs 94:192196d also discloses a benzoxazolone of the formula

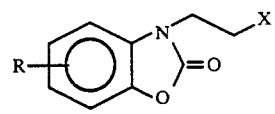

where X = CN, $CONH_2$, COHNPh, and states that this compound has antifungal activity. It should be noted that this compound does not possess a propargyl group.

SUMMARY OF THE INVENTION

We have found a new class of compounds having the general formula (I) as defined above, and the present invention is directed to those novel compounds and the preparation thereof. In another aspect the invention relates to the use of the compounds, or a composition containing said compounds, as a microbicide, and to microbicidal compositions containing the compounds.

The process for preparing the compounds of the invention comprises reacting a compound of the formula (III)

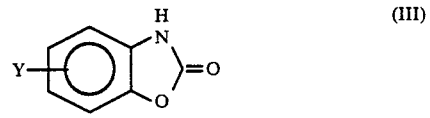

(III)

with a propargyl halide $X^1$—$CH_2$—C≡CH where $X^1$ is Br or Cl, and then halogenating the resulting product to produce a compound of the invention. An alternative process, also encompassed by the present invention, comprises first halogenating a propargyl halide $X^1$—$CH_2$—C≡CH and then reacting the halogenated product directly with compound (III) above.

DETAILED DESCRIPTION OF THE INVENTION AND PREFERRED EMBODIMENTS

As stated above, the compounds of the invention have the formula (I)

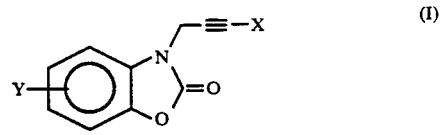

(I)

where
X = I or Br, and
Y = is independently selected from the group consisting of halogen, H, $NO_2$, ($C_1$-$C_4$)alkyl, ($C_1$-$C_4$)alkoxy, CN, OCO ($C_1$-$C_4$)alkyl, OCOPh or halo ($C_1$-$C_4$)alkyl.

Y may comprise a single substituent on the aromatic ring; alternatively the ring may be disubstituted with two Y substituents.

It is preferable that X is iodine: compounds in which Y is selected from H, chlorine and $NO_2$ are also preferred. Particularly preferred compounds include 3-(3-iodopropargyl)-2-benzoxazolone and 3-(3-iodopropargyl)-5-chloro-2-benzoxazolone.

Compositions comprising a compound according to formula I and either an agronomically acceptable carrier, a cosmetic agent, a cutting oil, a soap or synthetic detergent, a stabilizer, a film forming material, or the like have a wide range of utility for protecting against or controlling microorganisms from a wide variety of classes including fungus, bacteria, algae, viruses and yeasts. The preferred utilities of the compositions are to protect wood, agricultural crops, paint, adhesive, glue, paper, textile, leather, plastics, cardboard, lubricants, cosmetics, food, caulking, feed and industrial cooling water from microorganisms.

The following lists specific industries and applications of the compounds or compositions:

| Industry | Application |
| --- | --- |
| Adhesives, sealants | adhesives |
| | caulks |
| | sealants |
| Agriculture/food chain | adjuvant preservation |
| | agricultural active ingredient |
| | agricultural chemical preservative |
| | agricultural formulations preservation |
| | animal feed preservation |
| | dairy chemicals |
| | fertilizer preservation |
| | food preservation |
| | food processing chemicals |
| | grain preservation |
| | post-harvest produce protection |
| | sugar processing |
| | tobacco |
| Construction products | asphalt/concrete |
| | cement modifiers |
| | construction products |
| | roof mastics |
| | synthetic stucco |
| | wall mastics |
| | joint cement |
| Cosmetics and toiletries | cosmetics |
| | raw materials for cosmetics, toiletries |
| | toiletries |
| Disinfectants, antiseptics | antiseptic |
| | disinfectant |
| Emulsions, dispersions | aqueous dispersions |
| | dispersed pigments |
| | latex |
| | photographic emulsions |
| | pigment slurries |
| | polymer latices |
| Formulated household products | fabric softeners |
| | polishes |
| | waxes |
| | hand dish detergents |
| | raw materials |
| | liquid detergents |
| | hand soaps |
| Industrial processing, misc | electrodeposition paint, baths, rinses. |
| | electrodeposition pre-treatment, post rinses |
| | industrial fluids preservation |
| | pasteurization baths |
| | process aid preservation |
| Industrial water treatment | air washers |
| | cooling towers |
| | cooling water |
| | water cooling |
| | preservation/treatment of wooden cooling tower slats and structural members |
| | can warmers |
| | brewery pasteurization |
| | closed loop water cooling systems |
| Laundry | household laundry products |
| | laundered goods |
| | laundry rinse water |
| | sanitizers-laundry |
| Leather, leather products | leather and hide |
| | leather and hide products |
| Lubricants, hydraulic aids | automotive lubricants and fluids |
| | conveyor lubricants |
| | greases |
| | hydraulic fluids |
| | lubricants |
| Medical devices | diagnostic enzymes |
| | diagnostic kits |
| | medical devices |
| Metalworking & related app's | cutting fluids |
| | metal cleaning |
| | metalworking fluids |
| Odor control (active ingredient) | air conditioning |
| | animal bedding |
| | cat litter |
| | chemical toilet prep'ns |
| | deodorizers |
| | humidifiers |
| | industrial deodorants |
| | sanitary formulations |
| | toilet bowls |
| Paints and coatings | emulsions |
| | paints |
| Paper and wood pulp, their products | absorbent materials of paper and wood pulp |
| | packaging materials of paper and wood pulp |
| | paper |
| | paper products |
| | paper treatment |
| | soap wrap |
| | wood pulp |
| | wood pulp products |
| Paper mill | paper mill slimicides |
| | pulp and paper slurries |
| Petroleum refining, fuels | aviation fuels (jet fuel, aviation gas) |
| | crude oils |
| | burner, diesel and turbine fuel oils |
| | coat slurries |
| | diesel fuel additives |
| | diesel fuels |
| | fuels |
| | gasoline |
| | heating oils |
| | hydrocarbons |
| | kerosene |
| | liquefied petroleum gas |
| | petrochemical feedstocks |
| | petroleum products, storage, transportation and production |
| | recycled petroleum products |
| | residual fuel oils |
| | turbine oils |
| Photographic chemicals and process | photographic processing - wash water, rinses |
| | photoprocessing |
| | photoplate processing chemicals (developers, stabilizers etc) |
| Printing | fountain solutions (printing) |
| | ink components (pigments, resins, solvents, etc) |
| | inks |
| Sanitizers (active) | sanitizers |
| | sanitizers-dairy |
| | sanitizers-dental |
| | sanitizers-fermentation |
| | sanitizers-food preparation |
| | sanitizers-food processing |
| | sanitizers-medical |
| | sanitizers-rendering |
| | sanitizers-veterinary |
| Soaps, detergents, cleaners | cleaners |
| | detergents |

| Industry | Application |
|---|---|
| | household cleaners |
| | industrial cleaners |
| | liquid soaps |
| | oil and grease remover |
| | powdered soaps |
| | raw materials for cleaning products |
| | soaps |
| | surfactants |
| Textiles, textile products | bonded fabrics |
| | burlap |
| | canvas |
| | canvas goods |
| | carpet backing |
| | carpets |
| | clothing |
| | coated fabrics |
| | curtains |
| | draperies |
| | engineering textiles |
| | fibers |
| | geotextiles |
| | goods made of textiles |
| | knitted fabrics |
| | nets |
| | nonwoven fabrics |
| | rope |
| | rugs |
| | textile accessories |
| | textile products |
| | textiles |
| | upholstery |
| | woven fabrics |
| | yarn |
| Textile processing | dye fixatives |
| | dyes |
| | fiber lubricants |
| | hand modifiers |
| | sizes |
| | textile processing fluids |
| Therapeutic (active or preservative) | animal health/veterinary |
| | aquaculture |
| | dental |
| | human health |
| | pharmaceutical/therapeutic |
| Water purification | charcoal beds |
| | deionization resins |
| | filters |
| | membranes |
| | reverse osmosis membranes |
| | ultrafilters |
| | water purification |
| | water purification pipes, tubing |
| Wood applications | lazures (wood stains) |
| | wood |
| | wood products |
| Miscellaneous | alcohols |
| | bedding incorporating water of gels |
| | ceramic |
| | contact lens cases-leaching |
| | electronic circuitry |
| | electronics chemicals |
| | enzymes-food production |
| | enzymes |
| | enzymes-industrial |
| | gel cushions |
| | marine antifoulants |
| | mildewcides |
| | wood |
| | plastics |
| | laundry |
| | mining |
| | natural rubber latex |
| | oil field injection waters including enhanced recover injection fluids, drilling, fracturing and completion fluids |
| | pipes |
| | plastics |
| | polymer systems |
| | polymers and resins (synthetic and natural) |
| | reagent preservation |
| | rubber |
| | rubber products |
| | skin remover |
| | solid protective/decorative films |
| | stains |
| | swimming pools |
| | waste treatment |
| | water beds |

The amounts of the compound to be used depend on the application. The useful amounts for a particular application are similar to amounts used for other microbicide compounds. Typically, a composition may contain anything from 0.001 to 99.99% by weight of the compound; more usually from 0.01 to 5%.

The compound can be used in combination with other microbicides. The term "microbicide" is considered equivalent to "antimicrobial" as used herein.

When used as agricultural fungicides, the compounds of the invention can be applied as fungicidal sprays by methods commonly employed, such as conventional high-gallonage hydraulic sprays, low-gallonage sprays, air-blast, aerial sprays and dusts. The dilution and rate of application will depend upon the type of equipment employed, the method and frequency of application desired and diseases to be controlled, but the effective amount is usually from about 0.01 kilogram (kg) to about 20 kg, preferably from about 0.1 to about 5 kg and more preferably from about 0.125 to about 0.5 kg of active ingredient per hectare.

As a seed protectant, the amount of toxicant coated on the seed is usually at a dosage rate of about 10 to about 250 grams (g) and preferably from about 20 to about 60 g per 50 kilograms of seed. As a soil fungicide, the chemical can be incorporated in the soil or applied to the surface usually at a rate of 0.5 to about 20 kg and preferably about 1 to about 5 kg per hectare. As a foliar fungicide, the pyridazinone is usually applied to growing plants at a rate of about 0.1 to about 5 and preferably from about 0.125 to about 0.5 kg per hectare.

The compounds of the present invention are useful for the control of fungi and can be utilized at various loci such as the seed, the water surface, the soil or the foliage. For such purposes, these compounds can be used in the technical or pure form as prepared, as solutions or as formulations. The compounds are usually taken up in a carrier or are formulated so as to render them suitable for subsequent use as fungicides. For example, these chemical agents can be formulated as wettable powders, dry powders, emulsifiable concentrates, dusts, granular formulations, aerosols, or flowable emulsion concentrates. In such formulations, the compounds are extended with a liquid or solid carrier and when desired suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in McCutcheon's Emulsifiers and Detergents, McCutcheon's Emulsifiers and Detergents/-Functional Materials and McCutcheon's Functional Materials all published annually by McCutcheon Division of MC Publishing Company (New Jersey).

In general, the compounds utilized in this invention can be dissolved in appropriate solvents such as acetone, methanol, ethanol, dimethylformamide or dimethyl sulfoxide and such solutions extended with water. The concentrations of the solution can vary from 1% to 90% with a preferred range being 5 to 50%.

For the preparation of emulsifiable concentrates, the compounds of the invention can be dissolved in suitable organic solvents or a mixture of solvents, together with an emulsifying agent which permits dispersion of the fungicide in water. The concentration of the active ingredient in emulsifiable concentrates is usually 10% to 90% and in flowable emulsion concentrates; this can be as high as 75%.

Wettable powders suitable for spraying can be prepared by admixing the compound with finely divided solid, such as clays, inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%. A typical wettable powder is made by blending 50 parts of 3-(3-iodopropargyl)-5-chloro-2-benzoxazolone, 45 parts of a synthetic precipitated hydrated silicon dioxide sold under the trademark Hi-Sil® and 5 parts of sodium lignosulfonate (Marasperse® N-22). In another preparation of a Kaolin type, (Barden) clay is used in place of the Hi-Sil in the above-wettable powder and in another such preparation 25% of the Hi-Sil is replaced with a synthetic sodium silico aluminate sold under the trademark Zeolex® 7.

Dusts are prepared by mixing the compounds of the invention with finely divided inert solids which can be organic or inorganic in nature. Materials useful for this purpose include botanical flours, silicas, silicates, carbonates and clays. One convenient method for preparing a dust is to dilute a wettable powder with a finely divided carrier. Dust concentrates containing 20% to 80% of the active ingredient are commonly made and are subsequently diluted to 1% to 10% use concentration.

The compounds of the present invention may be utilized in combination with other fungicides such as:

(a) dithiocarbamate and derivatives such as: ferbam, ziram, maneb, mancozeb, zineb, propineb, metham, thiram, the complex of zineb and polyethylene thiuram disulfide, dazomet, and mixtures of these with copper salts;

(b) nitrophenol derivatives such as: dinocap, binapacryl, and 2-sec-butyl-4,6-dinitrophenyl isopropyl carbonate;

(c) heterocyclic structures such as: captan, folpet, glyodine, anilazine, ditalimfos, 4-butyl-1,2,4-triazole, 5-amino-1-[bis(dimethylamino)phosphinyl]-3-phenyl-1,2,4-triazole, etradiazole, dithianon, thioquinox, benomyl, thiabendazole, 4-(2-chlorophenylhydrazono)-3-methyl-5-isoxazolone, vinclozolin, iprodione, procymidone, triadimenol, triadimefon, bitertanol, prochloraz, fenarimol, bis-(p-chlorophenyl)-3-pyridinemethanol, bis-(p-chlorophenyl)-5-pyrimidinemethanol, triarimol, flutriafol, flusilazole, propiconazole, ectaconazole, myclobutanil, alpha-[2-(4-chlorophenyl)ethyl]-alpha-phenyl-1H-1,2,4-triazole-1-propanenitrile, hexaconazole, cyproconazole, terbuconazole, diniconazole, fluoroimide, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, cis-N-[(1,1,2,2-tetrachloroethyl)thiol]-4-cyclohexene-1,2-dicarboximide, cycloheximide, dehydroacetic acid, captafol, ethirimol, quinomethionate, D,L-methyl-N-(2,6-dimethylphenyl)-N-(2'-methoxyacetyl) alanine methyl ester, D,L-methyl-N-(2,6-dimethylphenyl)-N-chloroacetyl-D,L-2 aminobutyrolactone, D,L-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-(methoxymethyl)-1,3-oxazolidi-2,4-dione, 3-(3,5-dichlorophenyl)-1-isopropylcarbamoylhydantoin, 2-cyano-[N-(ethylaminocarbonyl)-2-methoximino]acetamide, fenpropimorph, fenpropidine, 2,6-dimethyl-N-tridecylmorpholine, dodemorph, and triforine;

(d) miscellaneous halogenated fungicides such as: chlorothalonil, dichlone, chloroneb, tricamba, TCPN, dichloran, 2-chloro-1-nitropropane, polychloronitrobenzenes such as pentachloronitrobenzene (PCNB), and tetrafluorodichloroacetone;

(e) fungicidal antibiotics such as: griseofulvin, kasugamycin, polyoxin, validamycin, and streptomycin;

(f) copper-based fungicides such as: copper hydroxide, cuprous oxide, basic cupric chloride, basic copper carbonate, copper terephthalate, copper naphthenate and Bordeaux mixture; and (g) miscellaneous fungicides such as: dodine, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, thiophanate-methyl, flutolanil, edinophos, isoprothiolane, propenazole, and tricyclazole.

SYNTHESIS

The compounds (I) of the present invention may be prepared by the following reaction:

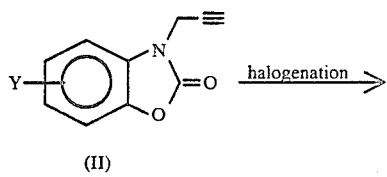

(II)

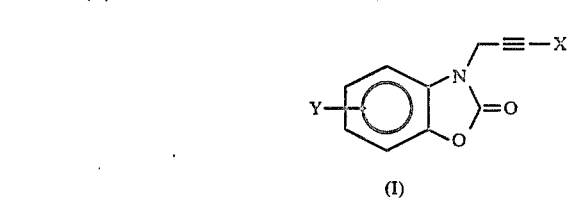

(I)

A variety of halogenation reactions may be utilized to prepare compounds of formula (I). One useful method is described here. A solution or suspension of compounds of formula (II) in solvents such as acetone, methyl ethyl ketone, or tetrahydrofuran is allowed to react with N-bromosuccinimide or N-iodosuccinimide in the presence of a catalyst such as silver nitrate. The reaction usually takes place within a range of from 20 min. to 24 hrs. The reaction is usually conducted at between 0° C. and 25° C.

The compounds of formula (II) may be prepared by the following reaction:

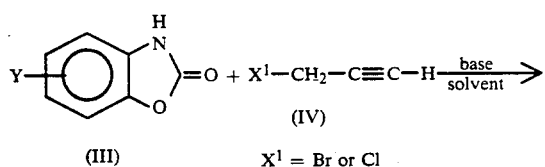

(III)    X¹ = Br or Cl

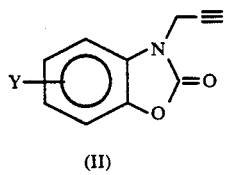

(II)

A solution or suspension of a compound of formula (III) in a solvent such as acetone or methyl ethyl ketone is treated with a base such as potassium carbonate or sodium carbonate followed by a propargylating agent such as propargyl bromide or propargyl chloride of formula (IV). The above treatment is usually conducted at room temperature under inert atmosphere such as nitrogen with stirring. The reaction mixture is then refluxed for a time ranging from 1 hr to 24 hr depending on the particular identity of compound (III). The reaction mixture is then cooled to room temperature and worked-up in a standard way. The reagents of formula (IV) are generally commercially available or can be prepared by using methods described in literature. The starting materials of formula (III) are also commercially available or can be prepared by using methods described in literature.

The compounds of the invention can also be prepared in one step from compounds of formula (III) by reacting them with a halopropargylating agent such as 3-iodopropargyl bromide or 3-iodopropargyl chloride in the presence of a base such as sodium carbonate or potassium carbonate. The reaction sequence may be depicted as follows:

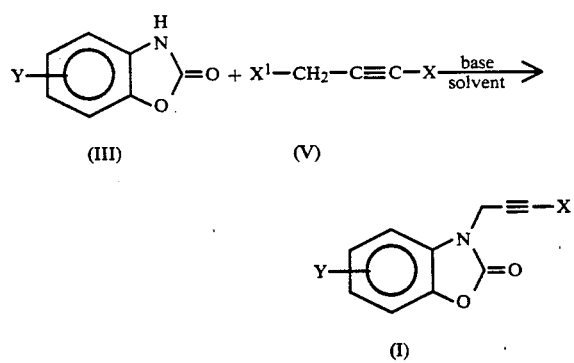

The compounds of formula (V) can be prepared from a method described in literature as follows:

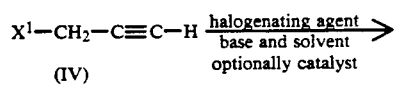

$X^1-CH_2-C\equiv C-X$ (V)

EXAMPLES

The following, non-limiting examples are presented to illustrate a few embodiments of the invention.

EXAMPLE 1

Preparation of 3-(3-iodopropargyl)-2-benzoxazolone.

In a 2 liter round bottom flask, equipped with a mechanical stirrer, a condenser and a drying tube on the top of the condenser, were placed benzoxazolone (20 g, 0.148 mole), dry acetone (575 ml), anhydrous potassium carbonate (40.9 g, 0.296 mole), and propargyl bromide (80% in toluene, 26 g, 0.175 mole). The reaction mixture was refluxed for 24 hr with stirring. The reaction mixture was cooled down to room temperature and filtered, and the filtrate concentrated to a brown residue. After crystallization with methylene chloride/hexane, a tan solid was obtained yielding 22.8 g (89%). m.p. 96°-98° C. An NMR spectrum showed the desired intermediate, 3-propargyl-benzoxazol-2-one.

To the solution of 3-propargyl-benzoxazol-2-one (7 g, 0.04 mole) in dry acetone (100 ml) in a 300-ml round bottom flask with magnetic stirring was added N-iodosuccinimide (11.1 g, 0.048 mole), followed by silver nitrate (0.3 g, 0.00176 mole). The reaction mixture was stirred at room temperature for 1 hr. The solid was filtered off and the filtrate concentrated on a rotary evaporator to give a residue. The crude solid was dissolved in ethyl acetate and washed with water and brine. The organic layer was dried over magnesium sulfate. After filtering the drying agent and evaporating the solvent, the resultant solid was crystallized from hexane/ethyl acetate yielding 9.1 g (75.8%) white solid, m.p. 162°-164° C. An NMR spectrum showed the desired compound.

EXAMPLE 2

Preparation of 3-propargyl-5-chlorobenzoxazol-2-one

In a 500-mL round bottom flask equipped with a magnetic stirrer, reflux condenser and a heating mantle were placed chlorzoxazone, or 5-chlorobenzoxazol-2-one, (10 g, 0.059 mole), potassium carbonate (9.8 g, 0.071 mole), propargyl bromide (10.5 g of 80% in toluene, 0.071 mole) and acetone (200 mL). The mixture was refluxed for 20 hours. The mixture was cooled down to room temperature and the solid was filtered off by suction-filtration. The filtrate was concentrated on a rotary evaporator to a solid residue. A pure, off-white product was obtained by crystallization from ethyl acetate hexane yielding 10.5 g (86%). m.p.

EXAMPLE 3

Preparation of 3-(3-iodopropargyl)-5-chlorobenzoxazol-2-one

In a 250-mL round bottom flask equipped with a magnetic stirrer and a nitrogen inlet were placed acetone (40 mL), 3-propargyl-5-chlorobenzoxazol-2-one (2 g, 9.64 mmole), silver nitrate (0.1 g, 0.59 mmole), and N-iodosuccinimide (2.4 g, 10.67 mmole). The mixture was stirred at room temperature for 5 hours. The resultant yellowish suspension was suction-filtered and the filtrate was concentrated on a rotary evaporator to give an off-white solid weighting 3.1 g (97%). m.p.=136°–140° C. An NMR spectrum showed the desired compound.

EXAMPLE 4

Preparation of 3-(3-bromopropargyl)-5-chlorobenzoxazol-2-one

In a 250-mL round bottom flask equipped with a magnetic stirrer and a nitrogen inlet were placed acetone (40 mL), 3-propargyl-5-chlorobenzoxazol-2-one (2 g, 9.64 mmole), silver nitrate (0.1 g, 0.59 mmole), and N-bromosuccinimide (1.9 g, 10.67 mmole). The mixture was stirred at room temperature for 5 hours. The resultant grey suspension was suction-filtered and the filtrate was concentrated on a rotary evaporator to give an off-white solid weighing 2.7 g (98%). m.p.=104°–106° C. An NMR spectrum showed the desired compound.

EXAMPLE 5

Other Species of Compounds of the Invention 1. 3-(3-iodopropargyl)-4-chlorobenzoxazol-2-one
2. 3-(3-iodopropargyl)-6-chlorobenzoxazol-2-one
3. 3-(3-iodopropargyl)-7-chlorobenzoxazol-2-one
4. 3-(3-iodopropargyl)-4-methylbenzoxazol-2-one
5. 3-(3-iodopropargyl)-5-methylbenzoxazol-2-one
6. 3-(3-iodopropargyl)-6-methylbenzoxazol-2-one
7. 3-(3-iodopropargyl)-7-methylbenzoxazol-2-one
8. 3-(3-iodopropargyl)-4-bromobenzoxazol-2-one
9. 3-(3-iodopropargyl)-5-bromobenzoxazol-2-one
10. 3-(3-iodopropargyl)-6-bromobenzoxazol-2-one
11. 3-(3-iodopropargyl)-7-bromobenzoxazol-2-one
12. 3-(3-iodopropargyl)-4-fluorobenzoxazol-2-one
13. 3-(3-iodopropargyl)-5-fluorobenzoxazol-2-one
14. 3-(3-iodopropargyl)-6-fluorobenzoxazol-2-one
15. 3-(3-iodopropargyl)-7-fluorobenzoxazol-2-one
16. 3-(3-iodopropargyl)-5,6-dichlorobenzoxazol-2-one
17. 3-(3-iodopropargyl)-6-methoxybenzoxazol-2-one
18. 3-(3-iodopropargyl)-6-nitrobenzoxazol-2-one
19. 3-(3-iodopropargyl)-4-nitro-6-fluorobenzoxazol-2-one
20. 3-(3-iodopropargyl)-4,5,7-trichlorobenzoxazol-2-one
21. 3-(3-iodopropargyl)-5-ethoxybenzoxazol-2-one
22. 3-(3-iodopropargyl)-5-cyanobenzoxazol-2-one
23. 3-(3-iodopropargyl)-5,6-dimethylbenzoxazol-2-one
24. 3-(3-iodopropargyl)-5,6-dimethoxybenzoxazol-2-one
25. 3-(3-iodopropargyl)-4-methoxybenzoxazol-2-one
26. 3-(3-iodopropargyl)-5-methoxybenzoxazol-2-one
27. 3-(3-iodopropargyl)-7-methoxybenzoxazol-2-one
28. 3-(3-iodopropargyl)-5-nitrobenzoxazol-2-one
29. 3-(3-iodopropargyl)-4-nitrobenzoxazol-2-one
30. 3-(3-iodopropargyl)-6-ethoxybenzoxazol-2-one
31. 3-(3-iodopropargyl)-4-ethoxybenzoxazol-2-one
32. 3-(3-iodopropargyl)-5-trifluoromethylbenzoxazol-2-one
33. 3-(3-iodopropargyl)-6-trifluoromethylbenzoxazol-2-one
34. 3-(3-iodopropargyl)-5,7-dichlorobenzoxazol-2-one
35. 3-(3-iodopropargyl)-5,7-dibromobenzoxazol-2-one
36. 3-(3-iodopropargyl)-5,7-dimethylbenzoxazol-2-one
37. 3-(3-iodopropargyl)-5-t-butylbenzoxazol-2-one
38. 3-(3-iodopropargyl)-5-chloro-6-bromobenzoxazol-2-one The following examples demonstrate the microbicidal activity of certain compounds of the invention: 3-(3-iodopropargyl)-2-benzoxazolone ($Y=H_1 X=I$), 3-(3-iodopropargyl)-5-chloro-2-benzoxazolone ($Y=Cl$, $X=I$), 3-(3-bromopropargyl)-5-chloro-2-benzoxazolone ($Y=Cl$, $X=Br$), and 3-(3-bromopropargyl)-2-benzoxazolone ($Y=H$, $X=Br$).

EXAMPLE 6

In Vitro Bactericidal and Fungicidal Evaluations

Activity against certain bacteria and fungi was determined using a minimum inhibitory concentration (MIC) test, which establishes the minimum concentration of test compound required to achieve complete inhibition of growth of the test organism.

An MIC value was obtained using a broth, two-fold serial dilution test performed as follows: A stock solution or dispersion of the test compound at a concentration of 1%, was made in a 5:3:2 solvent solution of acetone, methanol, and water. A volume of the stock solution was dispensed into culture media to give an initial starting test concentration of 500 ppm compound.

When the test was ready to be done, each vessel in the dilution series, except the first vessel, contained an equal volume of compound free broth. The first vessel contained twice the volume of broth with the starting concentration of test compound. One half of the broth from the first vessel was transferred to the second vessel. After being mixed, one half the resulting volume was removed from the second vessel and transferred to the third vessel. The entire cycle was repeated sufficiently to give a series of concentrations amounting to 500, 250, 125, 63, 31, 16, 8, and 4 ppm (or 25, 12.5, 6.2, 3.1, 1.6, 0.8, 0.4, 0.2), respectively.

Each vessel was then inoculated with a cell suspension of the appropriate test organism. Bacteria were grown in broth and fungi on agar slants for a time and at a temperature appropriate to the species being tested. At the end of the growth period, the bacteria containing broth was vortexed to disperse the cells. In the case of fungi, the spores were harvested by pipetting water onto the slant and dislodging the spores with a sterile loop. The cell/spore suspension was standardized by controlling incubation time, temperature, and the volume of the diluent. The suspension was then used to inoculate the vessels containing the broth compound. The vessels were then incubated at the appropriate temperature. After the incubation, the vessels were examined for growth/no growth. The minimum inhibitory concentration (MIC) is defined as the lowest concentration of compound that results in complete inhibition of growth of the test organism.

The organisms tested were bacteria *Pseudomonas fluorescens* (*Ps. fl*)-ATCC 948, *Pseudomonas aeruginosa* (*Ps. ae.*)-ATCC 15442, *Escherichia coli* (*E. coli*)-ATCC 11229, and *Staphylococcus aureus* (*S. aur*)-ATCC 6538; and fungi *Aspergillus niger* (*A. niger*)-ATCC 6275, *Penicillium funiculosum* (*P. fun.*)-ATCC 11797, *Cladosporium resinae* (*A. res.*)-ATCC 52833, *Aureobasidium pullulans* (*A. pull.*)-ATCC 9248, *Gloeophyllum trabeum* (*G. trab.*)-ATCC 11539; and two yeasts *Sacharomyces cereresae* (*S. cer.*)-ATCC 560, and *Rhorotorularubra* (*R. rubra*)-ATCC 2503.

| Results | MIC (ppm) for each compound | | | |
| --- | --- | --- | --- | --- |
| ORGANISM | Y = H, X = I | Y = 5-Cl, X = I | Y = 5-Cl, X = Br | Y = H, X = Br |
| Ps.fl | >250 | 16 | >250 | >250 |
| Ps.ae | >250 | >250 | >250 | >250 |
| E. Coli | >250 | >250 | >250 | >250 |
| S. aur | >250 | 16 | >250 | >250 |
| A. niger | <0.13 | <0.13 | 32 | >25 |
| A. pull | 0.25 | ≦1 | 32 | >25 |
| P. fun | ≦1 | ≦1 | >25 | >25 |
| Cl. res. | ≦5 | ≦1 | >25 | >25 |
| G. trab. | ≦0.2 | ≦1 | >25 | >25 |
| S. cer | ≦1 | ≦5 | >25 | >25 |
| R. rubra | ≦1 | ≦1 | >25 | >25 |

EXAMPLE 7

In Vitro Plant Fungicidal Tests

The effectiveness of three of the four compounds tested above at controlling selected plant fungi was tested by the following method.

The organisms employed in the test were:
PYU *Pythium ultimum* (Oomycete)
PHY *Phytophthora capsici* (Oomycete)
PIR *Piricularia oryzae* (Ascomycete)
HEL *Cochliobolus sativus* (Ascomycete)
BOC *Botrytis cinerea* (Ascomycete)
FUS *Fusarium roseum* (Ascomycete)
SEP *Septoria nodorum* (Ascomycete)
RHI *Rhizoctonia solani* (Basidiomycete)
XAN *Xanthomonas campestris* (bacterium)

Method

1. Culture maintenance: All 8 fungi and the bacterium used in this test were transferred and maintained on potato dextrose agar plates (2 plates/organism). Organisms were used at the following ages: a. 1 week old: PYU, PHY, RHI; b. 2 weeks old: XAN, PIR, BOC, HEL, FUS, SEP, COL, MON, CER, UST, ALT; c. 3 weeks old: PSH, VEN. *Pythium ultimum* and *Phytophthora capsici* were transferred to asparagine-sucrose broth shake cultures (ASB). *Rhizoctonia solani*, *Fusarium roseum*, and *Xanthomonas campestris* were maintained in yeast extract-dextrose broth (YDB) on a shaker. Culture flasks were inoculated with 6 mycelial plugs each (except for Pythium which was inoculated with only 3 plugs) taken from PDA plates. All liquid shaker cultures were used after 2 days growth.

2. Inoculum preparation. Conidia and mycelium from PIR, BOC, HEL, SEP, COL, MON, CER, PSH, UST and ALT were lightly scraped off into YDB so that mostly conidia are used as inoculum. XAN broth culture was poured (1 ml culture/100 ml broth) into YDB. PYU, PHY, RHI and FUS cultures were ground up and all but Pythium and Phytophthora filtered. Ten ml of the culture solutions of *R. solani* and *F. roseum* were added to 90 ml of YDB and 10 ml of the *P. capsici* was added to 90 ml ASB. Two ml of the culture solution of *P. ultimum* was added to 98 ml of ASB. 175 μl (single dose) or 100 μl (dose-response test) of inoculum broth was placed in each well of microtiter plates. The plates with inoculated media were refrigerated overnight.

3. Addition of test compound. 10 Mg a.i. (active ingredient) of the test compound was placed in 1 ml 1:1 acetone:methanol. 5 Microliters of this solution was pipetted into the microtiter plates containing 245 microliters of sterile water according to the grid. 25 Microliters of the resulting solution was transferred to the inoculated plates. The results below are reported as % disease control relative to untreated check plants.

| Compound | Dose (ppm) | % DISEASE CONTROL | | | | | | | | |
| --- | --- | --- | --- | --- | --- | --- | --- | --- | --- | --- |
| | | BOC | FUS | HEL | PHY | PIR | PRU | RMI | SEP | XAN |
| Y = H, X = I | 25 | 100 | 100 | 100 | 100 | 100 | 100 | 95 | 100 | 0 |
| Y = 5-Cl, X = I | 25 | 100 | 100 | 100 | 100 | 100 | 95 | 100 | 100 | 0 |
| Y = 5-Cl, X = Br | 25 | 50 | 0 | 50 | 0 | 0 | 50 | 0 | 0 | 0 |

EXAMPLE 8

In Vivo Plant Disease Control Tests 3-(3-Iodopropargyl)-2-benzoxazolone was tested for fungicidal activity in vivo against cucumber downy mildew (CDM), rice blast (RB), wheat glume blotch (WGB), tomato late blight (TLB), wheat powdery mildew (WPM), wheat stem rust (WSR) and wheat leaf rust (WLR). In tests on cereals (except for rice plants used for testing rice blast), the plants were trimmed about 24 hours prior to the application of the fungicide compound to provide a uniform plant height and to facilitate uniform application of the compound and inoculation with the fungus. The test compound was dissolved in a 2:1:1 mixture of water, acetone, and methanol, sprayed onto the plants, allowed to dry (four to six hours), and then the plants were inoculated with the fungus. Each test utilized control plants which were sprayed with the water, acetone, and methanol mixture and inoculated with the fungus. The remainder of the technique of each of the tests is given below and the results are reported as percent disease control (percentages of plants treated with the compounds of the present invention lacking disease signs or symptoms compared to the untreated control plants).

Cucumber Downy Mildew (CDM)

*Pseudoperonospora cubensis* was maintained on leaves of live Marketer cucumber plants in a constant temperature room at 65° F. to 75° F. in humid air with moderate light intensity for 7 to 8 days. A water suspension of the spores from infested leaves was obtained and the spore concentration was adjusted to about 100,000 per ml of water.

Marketer cucumber seedlings were inoculated by spraying the underside of the leaves with a DeVilbiss atomizer until small droplets were observed on the leaves. The inoculated plants were incubated in a mist chamber for 24 hours at about 70° F. and then subsequently incubated for 6 to 7 days in a controlled temperature room under mist at 65° F. to 75° F. Seven days after inoculation, the percent disease control was determined.

Rice Blast (RB)

Nato rice plants were inoculated with *Piricularia oryzae* (about 20,000 conidia per ml) by spraying the leaves and stems with an airbrush until a uniform film of inoculum was observed on the leaves. The inoculated plants were incubated in a humid environment (75° F. to 85° F.) for about 24 hours, then placed in a greenhouse environment (70° F. to 75° F.). Seven to eight days after inoculation, the percent disease control was determined.

Wheat Glume Blotch (WGB):

*Septoria nodorum* was produced by incubating plates containing sporulating mycelium for 48 hours in darkness at 20° C. until a white mycelium was observed. The plates were then incubated at 21° C. under continuous light for 15-20 days, at which stage the mycelium had a pink color.

A suspension of spores in deionized water was adjusted to a concentration of 150-300 spores/ml. Wheat plates were inoculated by spraying the leaves with the spore suspension using a hand sprayer, optionally after spraying the plants with a light mineral oil and waiting 5 minutes. The inoculated plants were incubated for 72 hours in a humidity cabinet at 20° C. with a photoperiod of 16 hours light/8 hours dark. The plants were then placed in a growth chamber for 7-9 days at 20° C. with 16 hours light/8 hours dark, before percent disease control was evaluated.

Tomato Late Blight (TLB)

*Phytophthora infestans* was cultured on four week old Pixie tomato plants in a controlled environment room (65° F. to 70° F. and 100% relative humidity). After storage, the spores were washed from the leaves with water and dispersed by DeVilbiss atomizer over three week old Pixie tomato plants which had been sprayed previously with experimental fungicides. The inoculated plants were placed in a humidity cabinet at 70° F. and constant mist for 24 hours for infection. The plants were then moved to the controlled environment room as above and scored after three more days incubation. Disease control levels were recorded as percent control four days after inoculation and five days after spraying the compounds.

Wheat Powdery Mildew (WPM)

*Erysiphe graminis* (f. sp. *tritici*) was cultured on Pennol wheat seedlings in a controlled temperature room at 65° F. to 75° F. Mildew spores were shaken from the culture plants onto Pennol wheat seedlings which had been sprayed previously with the fungicide compound. The inoculated seedlings were kept in a controlled temperature room at 65° F. to 75° F. and subirrigated. The percent disease control was rated 8 to 10 days after the inoculation.

Wheat Stem Rust (WSR)

*Puccinia graminis* (f. sp. *tritici* Race 15B-2) was cultured on Wanzer wheat seedlings for a period of 14 days in a greenhouse. A water suspension of the spores from infested plants was obtained and the spore concentration was adjusted to about 200,000 spores per ml of deionized water. Wanzer wheat plants which had been previously treated with the fungicide compounds were inoculated by applying the stem rust spore suspension, until runoff, with a DeVilbiss atomizer at 5 lbs. per square inch air pressure. After inoculation, the plants were placed in a humid environment at approximately 75° F. where they were exposed to 12 hours of continuous darkness followed by a minimum of 3 to 4 hours of light having an intensity of about 500 footcandles. The temperature in the chamber did not exceed 85° F. At the end of the light period, the plants were placed in a greenhouse where they were permitted to grow for a period of two weeks at which time the percent disease control was determined. *Wheat Leaf Rust (WLR)*

*Puccinia recondita* (f. sp. *tritici* Races PKB and PLD) was cultured on seven day old wheat (cultivar Fielder) over a 14 day period in the greenhouse. Spores were collected from the leaves with a cyclone vacuum or by settling on aluminum foil. The spores were cleaned by sieving through a 250 micron opening screen and stored or used fresh. Storage employed sealed bags in an Ultralow freezer. When stored, spores were heat shocked for two minutes at 40° F. before use. A spore suspension was prepared from dry uredia by adding 20 mg (9.5 million) per ml of Soltrol oil. The suspension was dispensed into gelatin capsules (0.7 ml capacity) which attached to the oil atomizers. One capsule was used per flat of twenty of the two inch square pots of seven day old Fielder wheat. After waiting for at least 15 minutes for the oil to evaporate from the wheat leaves, the plants were placed in a dark mist chamber (18°-20° C. and 100% relative humidity) for 24 hours. The plants were then put in the greenhouse for the latent period and scored after 10 days for disease levels. Protective and curative tests were inoculated one day and two days after, respectively, before spraying the plants with the test chemicals.

|  |  | % DISEASE CONTROL | | | | | |
|---|---|---|---|---|---|---|---|
| COMPOUND | DOSE(PPM) | CDM | RB | WGB | TLB | WLR | WPM |
| Y = H, X = I | 200 | 50 | 95 | 0 | 0 | 90 | 90 |

I claim:
1. Compound of the formula (I)

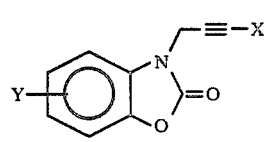

wherein
X is selected from the group consisting of I and Br; and

Y is independently selected from the group consisting of H, halogen, $NO_2$ ($C_1$-$C_4$) alkyl, ($C_1$-$C_4$) alkoxy, CN, $OCO(C_1$-$C_4)$alkyl, OCOPh, and halo ($C_1$-$C_4$) alkyl.

2. Compound according to claim 1 wherein X is I.

3. Compound according to claim 1 wherein Y is selected from the group consisting of H and chlorine.

4. Compound having the formula

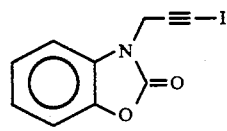

(II)

5. Composition comprising a compound according to claim 1 and a second component selected from the group consisting of an agronomically acceptable carrier, a cosmetic agent, a cutting oil, a metal-working fluid, a soap or a synthetic detergent, a stabilizer, and a film-forming material.

6. Composition according to claim 5 wherein the compound is present in an amount of from 0.01 to 5% by weight.

7. Composition according to claim 5 which is for microbicidal use.

8. Composition according to claim 5 which comprises an agriculturally acceptable carrier and a fungicidally effective amount of the compound.

9. A method for controlling fungus which comprises applying to the fungus or its habitat a fungicidally-effective amount of the compound of claim 1.

10. Process comprising the use of the compound of claim 1 as a microbicide.

11. Process according to claim 10 which comprises inhibiting the growth of bacteria, fungi or algae in a locus subject or susceptible to contamination thereby, by incorporating into or onto the locus a composition containing the compound of claim 1 in an amount which is effective to adversely affect the growth of said bacteria, fungi or algae.

* * * * *